United States Patent
Weinandy

(10) Patent No.: US 8,784,378 B2
(45) Date of Patent: Jul. 22, 2014

(54) DRUG DELIVERY DEVICE WITH LIGHT SOURCE

(75) Inventor: Ludwig Weinandy, Frankfurt (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/701,960

(22) PCT Filed: Jun. 6, 2011

(86) PCT No.: PCT/EP2011/059293
§ 371 (c)(1),
(2), (4) Date: Feb. 12, 2013

(87) PCT Pub. No.: WO2011/154355
PCT Pub. Date: Dec. 15, 2011

(65) Prior Publication Data
US 2013/0138040 A1    May 30, 2013

Related U.S. Application Data

(60) Provisional application No. 61/352,036, filed on Jun. 7, 2010.

(30) Foreign Application Priority Data

Sep. 2, 2010    (EP) ..................................... 10174993

(51) Int. Cl.
*A61M 5/00* (2006.01)

(52) U.S. Cl.
USPC ........................................................ 604/111

(58) Field of Classification Search
USPC .................................. 604/67, 87, 97.03, 111
See application file for complete search history.

(56) References Cited

U.S. PATENT DOCUMENTS

| | | | | |
|---|---|---|---|---|
| 5,954,700 | A * | 9/1999 | Kovelman | 604/232 |
| 6,110,152 | A * | 8/2000 | Kovelman | 604/232 |
| 7,749,186 | B2 * | 7/2010 | Kohlbrenner et al. | 604/67 |
| 2001/0034502 | A1 * | 10/2001 | Moberg et al. | 604/154 |
| 2002/0133114 | A1 * | 9/2002 | Itoh et al. | 604/67 |
| 2007/0021715 | A1 * | 1/2007 | Kohlbrenner et al. | 604/67 |
| 2007/0088271 | A1 | 4/2007 | Richards | |
| 2010/0204602 | A1 * | 8/2010 | Addington et al. | 600/538 |

FOREIGN PATENT DOCUMENTS

| | | |
|---|---|---|
| WO | 2007/107562 | 9/2007 |
| WO | 2009/015933 | 2/2009 |
| WO | 2010/089310 | 8/2010 |

OTHER PUBLICATIONS

International Search Report for Int. App. No. PCT/EP2011/059293, completed Jul. 21, 2011.

* cited by examiner

*Primary Examiner* — Nicholas Lucchesi
*Assistant Examiner* — Diva K Chander
(74) *Attorney, Agent, or Firm* — McDonnell Boehnen Hulbert & Berghoff LLP

(57) ABSTRACT

A visual identification coding for a cartridge or cartridge holder for use with a drug delivery device is described. The visual identification coding includes a cartridge containing a drug and a light source located on the cartridge to visually indicate that the correct cartridge has been inserted into the drug delivery device. The light source may be a light emitting diode (LED), a surface mount diode (SMD), or an organic light emitting diode (OLED). A cartridge holder may also be included to receive the cartridge. In another embodiment, the light source may be located on the cartridge holder or a dose setting member.

17 Claims, 5 Drawing Sheets

DRUG DELIVERY DEVICE WITH LIGHT SOURCE

CROSS REFERENCE TO RELATED APPLICATIONS

The present application is a U.S. National Phase Application pursuant to 35 U.S.C. §371 of International Application No. PCT/EP2011/059293 filed Jun. 6, 2011, which claims priority to U.S. Provisional Patent Application No. 61/352,036 filed Jun. 7, 2010 and European Patent Application No. 10174993.5 filed Sep. 2, 2010. The entire disclosure contents of these applications are herewith incorporated by reference into the present application.

FIELD OF INVENTION

The present disclosure is generally directed to reservoirs, particularly reservoirs containing a medicament. More particularly, the present disclosure is generally directed to a drug delivery device including a light source for identifying a type of drug for use with a reservoir and reservoir housing and ensuring the reservoir has been correctly inserted. As just one example, such medicament reservoirs may comprise an ampoule, a cartridge assembly, a vial, or a pouch, and may be used with a medical delivery device. Exemplary medical delivery devices include, but are not limited to syringes, pen type syringes, pumps, inhalers, or other similar injection or infusing devices that require at least one reservoir containing at least one medicament.

BACKGROUND

Medicament reservoirs such as ampoules, cartridge assemblies, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient loads a cartridge containing the insulin into a proximal end of a cartridge housing. After the cartridge assembly has been correctly loaded, the user may then be called upon to select a dose of medicament. Multiple doses may be dosed from the cartridge assembly. Where the drug delivery device comprises a reusable device, once the cartridge assembly is empty, the cartridge housing is disconnected from the drug delivery device and the empty cartridge is removed and replaced with a new cartridge. Most suppliers of such cartridges recommend that the user dispose of the empty cartridges properly. Where the drug delivery device comprises a disposable device, once the cartridge assembly is empty, the user is recommended to dispose of the entire device.

Such known self administration systems requiring the removal and reloading of empty cartridges have certain limitations. For example, in certain generally known systems, a user simply loads a new cartridge assembly into the delivery system without the drug delivery device or without the cartridge having any mechanism of preventing cross use of an incorrect cartridge. That is, the drug delivery device does not have a mechanism for determining if the medicament contained in the cartridge is indeed the correct type of medicament to be administered by the patient. Alternatively, certain known drug delivery devices do not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short acting insulin in lieu of a long acting insulin could result in injury or even death.

Another concern that may arise with such disposable cartridges is that these cartridges are manufactured in essentially standard sizes and manufactured to comply with certain recognized local and international standards. Consequently, such cartridges are typically supplied in standard sized cartridges (e.g., 3 ml cartridges). Therefore, there may be a variety of cartridges supplied by a number of different suppliers and containing a different medicament but they may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge. As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate or mechanically or electrically code a cartridge to its drug type and design an injection device that only accepts or works with the dedication or coded features provided on or with the cartridge so as to prevent unwanted cartridge cross use. Similarly, there is also a general need for a dedicated cartridge that allows the drug delivery device to be used with only an authorized cartridge containing a specific medicament while also preventing undesired cartridge cross use.

There is also a general need to provide a cartridge that is difficult to tamper with so that the cartridge may not be compromised in that the cartridge can be used with an unauthorized drug or drug delivery device. Because such cartridges may be difficult to copy, they may also reduce the risk of counterfeiting: i.e., making it more difficult for counterfeiters to provide unregulated counterfeit medicament carrying products.

It is an aim to provide means to reduce the potential risk of a user loading an incorrect drug type cartridge.

SUMMARY

This aim is achieved by a drug delivery device comprising a cartridge containing a drug; a cartridge holder to receive the cartridge and a light source to visually indicate that the correct cartridge or the correct cartridge holder has been inserted into the drug delivery device. The drug delivery device may be a device designed to dispense a selected dose of a drug, e.g. insulin, insulin analogues, growth hormones, heparins and their derivates etc., optionally suitable for self-administration. The dose may be fixed or variable. The device may be essentially of mechanical type or may comprise electronic elements for the drug and delivery operation or for indicating status information. The device may be a mobile, hand-held device, e.g. a drug delivery pen type device. The device is suitable for holding a cartridge containing a drug that can be administered via a needle, for example. One embodiment of the cartridge is manufactured of glass and includes a generally tubular barrel. The cartridge is held by a cartridge holder, which may be an integral part of a housing of the device, forming an inner bore of the drug delivery device which is suitable for holding the cartridge. Alternatively the cartridge and the cartridge holder may be formed as one piece, for example as injection molded polymer cartridge. "Inserting into the drug delivery device" may mean that the cartridge or the cartridge holder may be attached to at least one other part of the drug delivery device by any suitable means, for example by a snapping connection or a threaded connection, or that the cartridge or the cartridge holder are positioned so that they are held by at least any other part of the drug delivery device. In one embodiment the cartridge is held in a cavity formed by the cartridge holder, the cartridge holder being attached to a distal housing of the drug delivery device by snapping means, for example. The light source is suitable for visually indicating that the correct cartridge or the correct cartridge holder is inserted. Visual indication may be achieved by a lit light source. If the incorrect cartridge or the incorrect cartridge holder is inserted, the light source may be off. In other words, one state of the light source shows that the correct cartridge or the correct cartridge holder is inserted. Another state of the light source shows that the correct cartridge or the correct cartridge holder is not inserted. Correct cartridge may mean that the medicament contained in the cartridge is indeed the correct type of medicament to be administered by the patient. Alternatively, the correct cartridge may contain a type of medicament within the cartridge that should be used with a particular drug delivery system. The correct cartridge holder may be suitable for holding a cartridge type that should be used with a particular drug delivery system. The cartridge type may be used only for one medicament or one type of medicament. In other words, indication that the correct cartridge or the correct cartridge holder has been inserted into the drug delivery device means indication that the cartridge or the cartridge holder is a given type of the cartridge or the cartridge holder.

A visual identification coding for a cartridge or cartridge holder for use with a drug delivery device is described. The visual identification coding includes a cartridge containing a drug and a light source located on the cartridge to visually indicate that the correct cartridge has been inserted into the drug delivery device. The light source may be a light emitting diode (LED), an organic light emitting diode (OLED), or a surface mount diode (SMD), for example an LED or OLED which is supplied in a surface mounted device package. A cartridge holder may also be included to receive the cartridge. In another embodiment, the light source may be located on the cartridge holder or a dose setting mechanism.

According to an exemplary arrangement a drug delivery device is provided. The drug delivery device includes a cartridge containing a drug and a light source located on the cartridge to visually indicate to a user that the correct cartridge has been inserted into the drug delivery device. The light source may be a light emitting diode (LED), a surface mount diode (SMD), or an organic light emitting diode (OLED), for example. The light source may be activated by a trigger upon insertion of the correct cartridge into the drug delivery device. In one embodiment, the light source comprises a blue light source to indicate that the inserted cartridge is correct for the drug delivery device. The drug delivery device may further comprise a cartridge holder removably secured to the cartridge. In one embodiment, the light source includes one or more colored lights that indicate that a specific drug is contained in the cartridge. The light source may include at least two lights of different colors to indicate that a specific drug is contained in the cartridge. Alternatively, the light source comprises only one light. In another embodiment, the light source comprises a plurality of lights. The drug delivery device may further include a cartridge sleeve secured to the cartridge. One embodiment of the sleeve includes at least two conductive wires allowing a connection to a circuit for illuminating the light source.

In another arrangement, a drug delivery device is provided having a cartridge containing a drug and a cartridge holder to receive the cartridge, the cartridge holder including a light source to visually indicate that the correct cartridge holder has been inserted into the drug delivery device. The light source may comprise a light emitting diode (LED), a surface mount diode (SMD), or an organic light emitting diode (OLED). The drug delivery device may be activated by a trigger upon insertion of the cartridge into the drug delivery device. In one embodiment the light source comprises a blue light to indicate that the inserted cartridge holder is correct for the drug delivery device. One embodiment of the light source includes one or more colored lights that indicate that a specific drug is contained in the cartridge. The light source may include at least two lights of different colors to indicate that a specific drug is contained in the cartridge. Alternatively, the light source comprises only one light. In another embodiment, the light source comprises a plurality of lights. Moreover, the drug delivery device may further comprise a cartridge sleeve secured to the cartridge.

In yet another embodiment, a drug delivery device is provided having a cartridge containing a drug and a dose setting member to receive the cartridge, the dose setting member including a light source to visually indicate that the correct cartridge has been inserted into the drug delivery device. The dose setting member is a part of the device which comprises a dose setting and delivery mechanism which may be located in a distal part of the housing of the drug delivery device. In one embodiment, the light source is located on the housing of the dose setting member.

In one embodiment, a light source is provided on a drug delivery device, cartridge holder, or cartridge to provide a visual indication to a user that the correct drug cartridge and holder are being inserted into the correct drug delivery device. Further, the color of the light may indicate the type of drug contained in the cartridge. Thus, this feature ensures that the appropriate cartridge and drug can be correctly identified by the patient.

The terms "drug" and "medicament", as used herein, preferably mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta¬ decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

Figure 1A:
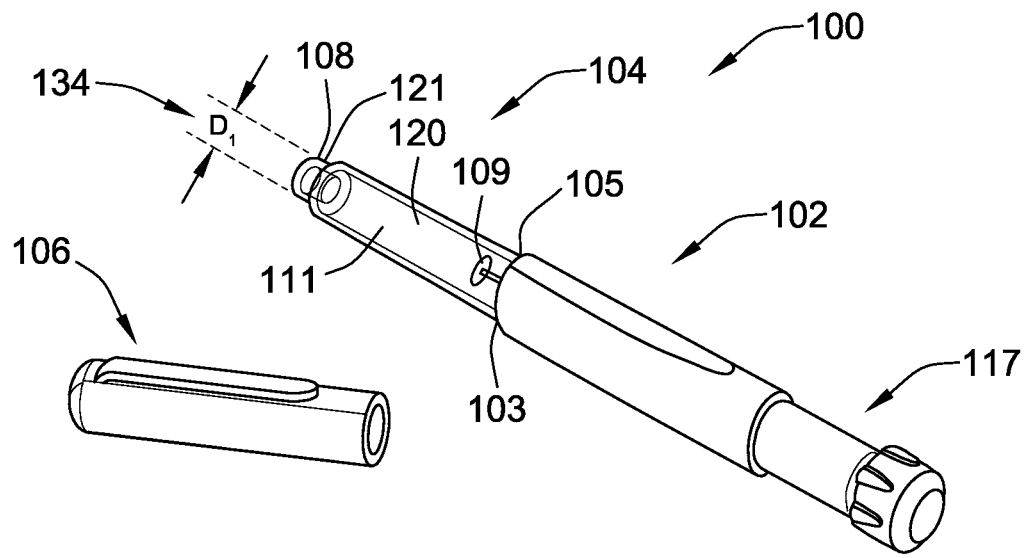
FIG. 1A illustrates an exemplary pen type drug delivery device.

Referring to FIG. 1A, there is shown a drug delivery device 100 in the form of a pen type syringe. The drug delivery device 100 comprises a dose setting member 102, a cartridge holder 104, and a removable cap 106. A proximal end 105 of the cartridge holder 104 and a distal end 103 of the dose setting member 102 are removably secured together. The dose setting member 102 comprises a piston rod 109, such as a threaded piston rod 109 that rotates when a dose is injected.

To inject a previously set dose, a double ended needle assembly (not shown) is attached to a distal end 108 of the cartridge holder 104. Preferably, the distal end 108 of the cartridge holder 104 comprises a thread 121 (or other suitable connecting mechanism such as a snap lock, snap fit, form fit, or bayonet lock mechanism) so that the needle assembly (not shown in FIG. 1A) may be removably attached to the distal end 108 of the cartridge holder 104. When the drug delivery device 100 is not in use, the removable cap 106 can be releasably retained over the cartridge holder 104.

Figure 1B:
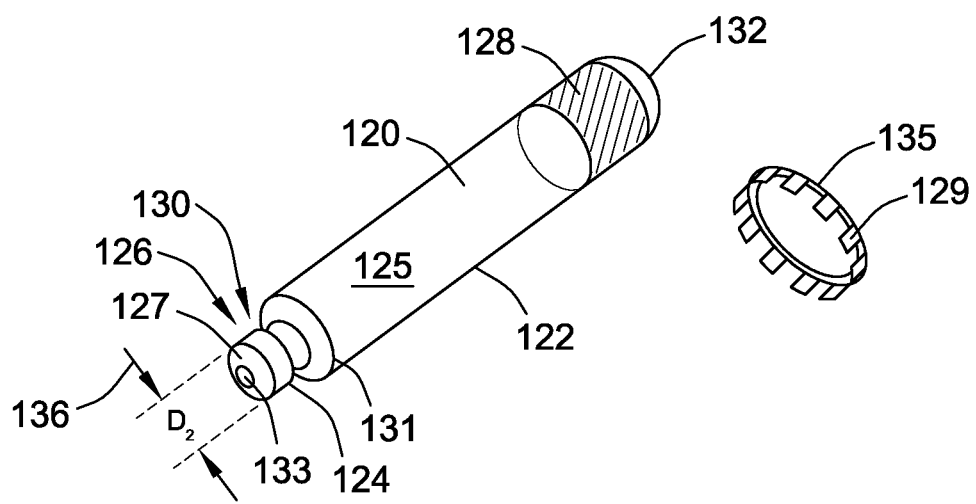
FIG. 1B illustrates an exemplary drug cartridge.

An inner cartridge holder cavity 111 defined by the cartridge holder 104 is dimensioned and configured to securely receive and retain a cartridge 120, such as glass cartridge 120. FIG. 1B illustrates a perspective view of the cartridge 120 that may be used with the drug delivery 100 device illustrated in FIG. 1A. Typically, the cartridge 120 is manufactured of glass and includes a generally tubular barrel 122 extending from a distal end 130 to a proximal end 132. The cartridge 120 may be inserted into an inner bore of the drug delivery device 100. The inner bore may be the inner cartridge holder cavity 111. An outer cartridge sleeve 129 may be secured to the cartridge 120. The cartridge sleeve 129 may include at least two conductive wires 135.

At the distal end 130, the cartridge 120 includes a smaller diameter neck 126 and this neck 126 projects distally from the shoulder 131 of the barrel 122. Preferably, the smaller diameter neck 126 is provided with a large diameter annular bead 124 which extends circumferentially thereabout at the extreme distal end of the neck 126 and defines an opening 127. A pierceable seal or septum 133 is securely held across the opening 127 by a metallic sleeve or a ferrule.

Medicament 125 is pre-filled into the cartridge 120 and is retained within this cartridge 120, in part, by the pierceable seal or septum 133, a ferrule, and a stopper 128. The stopper 128 is in sliding fluid-tight engagement with the inner tubular wall of the barrel 122. Axially directed forces acting upon the stopper 128 during dose injection or dose administration urge the medication 125 from the cartridge 120 though a double ended needle mounted onto the distal end 130 of the cartridge holder 104 and into the injection site. Such axially directed forces may be provided by the piston rod 109 working in unison with the dose setting member 102.

A portion of the cartridge holder 104 defining the cartridge holder cavity 111 is of substantially uniform diameter represented in FIG. 1A by D1 134. This diameter D1 134 is preferably slightly greater than the diameter D2 136 of the cartridge 120. The interior of the cartridge holder 104 includes an inwardly-extending annular portion or stop that is dimensioned to prevent the cartridge 120 from moving within the cartridge holder 104. In this manner, when the cartridge 120 is loaded into the cavity 111 of the cartridge holder 104 and the cartridge holder 104 is then connected to the dose setting member 102, the cartridge assembly will be securely held within the cartridge holder cavity 111. The cartridge holder 104 may also include a fastening mechanism for securing the cartridge holder 104 within the drug delivery device 100, which is described in more detail below.

A number of doses of a medicament 125 may be dispensed from the cartridge 120. Preferably, the cartridge 120 contains a type of medicament 125 that may be administered often, such as one or more times a day. One such medicament 125 is insulin.

The dose setting member 102 comprises a dose setter 117 at the proximal end of the dose setting member 102. In one preferred arrangement, the dose setter 117 is rotated to set a dose. To administer this set dose, the user attaches the needle assembly comprising a double ended needle on the distal end of the cartridge holder 104. In this manner, the needle assembly pierces the seal or septum 133 of the cartridge 120 and is therefore in liquid communication with the medicament 125. The user pushes on the dose setter 117 to inject the set dose. The same dose setting and dose administration procedure is followed until the medicament 125 in the cartridge 120 is expended and then a new cartridge 120 must be loaded in the drug delivery device. To exchange an empty cartridge 120, the user is called upon to remove the cartridge holder 104 from the dose setting member 102.

In accordance with exemplary embodiments, a cartridge, such as cartridge 120, a cartridge holder, such as cartridge holder 104, or a dose setting member, such as dose setting member 102, may include a visual indicator to indicate to a user that the correct cartridge 120 has been inserted into the drug delivery device 100.

Figure 2A:
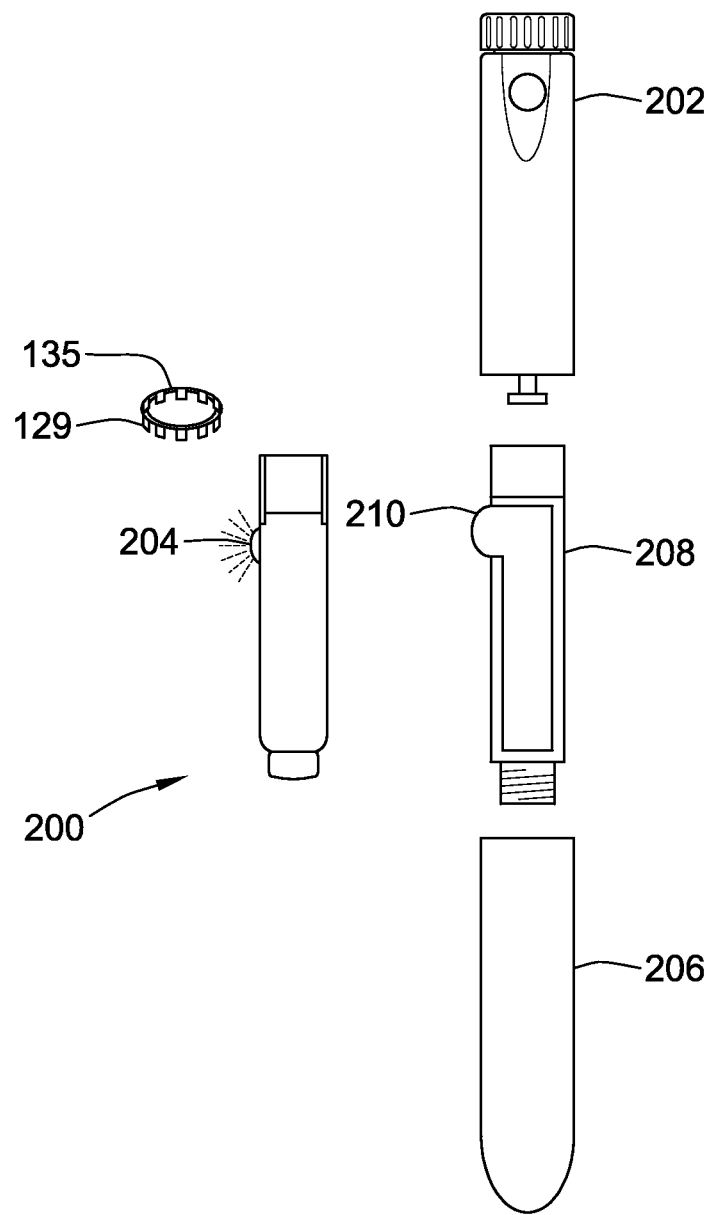
FIGS. 2A-G illustrate exemplary delivery devices having one or more light sources.

The following figures illustrate different embodiments having light sources 204. A light source 204 is provided on a drug delivery device 100, cartridge holder 208, or cartridge 200 to provide a visual indication to a user that the correct drug cartridge 200 and holder 208 are being inserted into the correct drug delivery device 100. Further, the color of the light may indicate the type of drug contained in the cartridge 200. Thus, this feature ensures that the appropriate cartridge 200 and drug can be correctly identified by the patient. FIG. 2A illustrates a first arrangement of a cartridge 200 including a visual indicator, such as a light source 204. This cartridge 200 may be connected to a drug delivery device, such as drug delivery device 100. The cartridge 200 is intended for use with a drug delivery device similar to the drug delivery device 100 of FIG. 1A, but a preferred drug delivery device for use with the cartridge 200 may have a slightly modified inner cavity. In other embodiments, the light source 204 may be located on the cartridge holder 208 or on the dose setting member 202.

Figure 3:
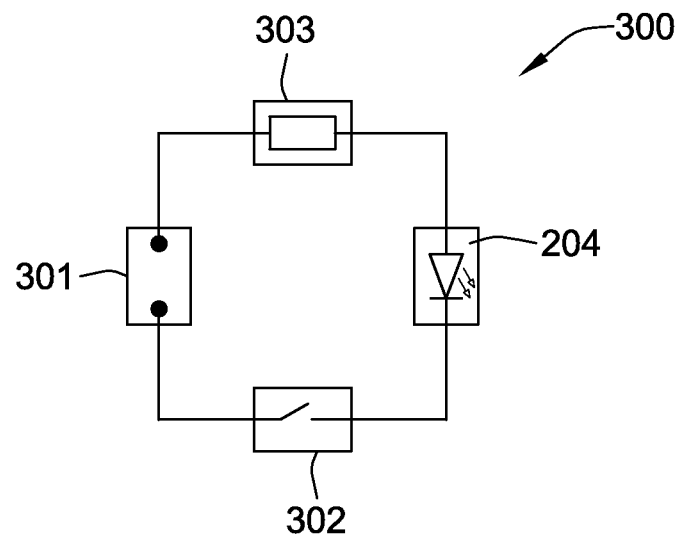
FIG. 3 illustrates a circuit diagram for controlling the operation of the light source.

FIG. 2A illustrates a first arrangement of a cartridge 200 for use with the drug delivery device 100. The cartridge 200 may also include a cartridge sleeve 129 to allow a connection by a conductive wire 135 to a circuit 300, which is shown in FIG. 3. The cartridge sleeve 129 may prevent insertion of an incorrect cartridge 200 into the drug delivery device 100 due to the dimension and shaping of the cartridge sleeve 129. Alternatively, any suitable coding included on the cartridge 200, cartridge holder 208, or dose setting member 202 may be used to ensure that the correct cartridge 200 is inserted into the correct drug delivery device 100.

In this arrangement, the visual indicator is a light source 204 located on the cartridge 200. The light source 204 is illuminated after a cartridge 200 is placed in the drug delivery device 100 and a switch has been activated. The cartridge 200 may be inserted into a cartridge holder 208, which is then inserted into the drug delivery device 100. The cartridge 200 may include a protrusion 210 to accommodate the light source 204. A removable cap 206 may be placed over the cartridge 200 and cartridge holder 208.

The light source 204 may indicate whether the correct cartridge 200 has been inserted into the drug deliver device 100 by the color of the light displayed. For example, a blue light may indicate that the correct insulin cartridge has been inserted into the drug delivery device 100. The light source 204 may illuminate only after insertion of the cartridge 200 and the locking of the cartridge holder 208 and the dose setting member 202, to indicate that the drug delivery device 100 is ready for an injection. The light source 204 may be activated by a trigger, such as by pushing a button or turning a knob to a start position, for example. Thus, this system helps to ensure that the appropriate cartridge 200 and drug can be correctly identified by the patient. In an alternate embodiment, a red light may indicate that the drug delivery device 100 is not ready for use or that an incorrect cartridge 200 has been inserted.

The light source 204 may be a light emitting diode (LED). In an alternative embodiment, the light source 204 may be an SMD or an OLED. The light source 204 may be secured to the cartridge 200, the cartridge holder 208, or the dose setting member 202. The light source 204 may be glued onto the cartridge 200 or the cartridge holder 208. Alternatively, the light source 204 may be secured to the cartridge 200, cartridge holder 208, or dose setting member 202 by any suitable fastening mechanism. In yet another embodiment, the light source 204 may be constructed as an integral part of the cartridge sleeve 129.

The light source 204 may comprise a number of different features, either alone or in combination. For example, the features may comprise a single light or multiple lights. The features may also include a particular color light, such as a blue light to indicate that the correct drug or cartridge 200 has been inserted into the correct drug delivery device 100. Further, the color of the light or combinations of colors and lights used may correspond to the type of drug contained in the cartridge 200.

Additional features which may be included as characteristics of the light source 204 are the size, shape, and orientation of the light source 204. For example, the light source 204 may be large or small, and may be located anywhere along the cartridge 200, cartridge holder 208, or dose setting member 202. As another example, a series of diodes may be used to demonstrate to the user the progress of the injection.

The cartridge 200 may be received by a cartridge holder, such as cartridge holder 208. When the light source 204 is illuminated, this provides an indication to the user or health care provider that the appropriate cartridge holder 208 has been paired with the appropriate cartridge 200, and to the appropriate drug delivery device 100.

Figure 2B:
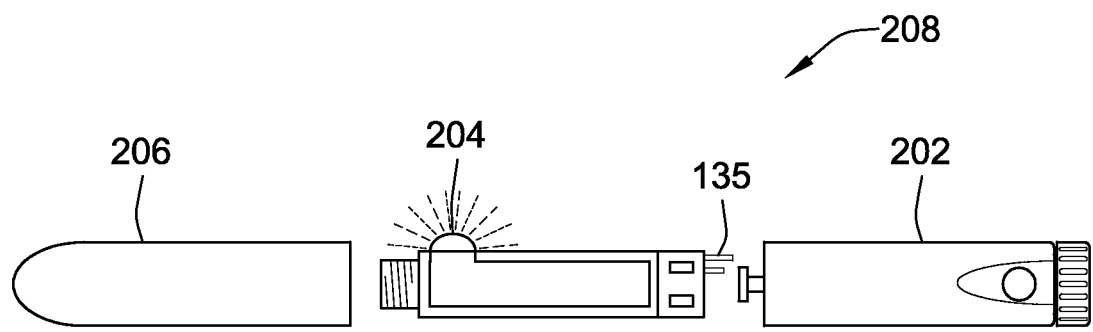
Figure 2C:
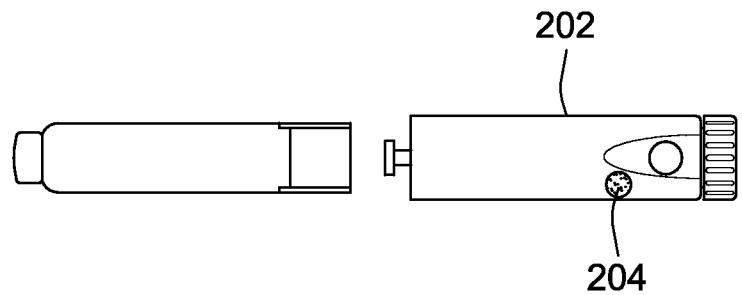
Figure 2D:
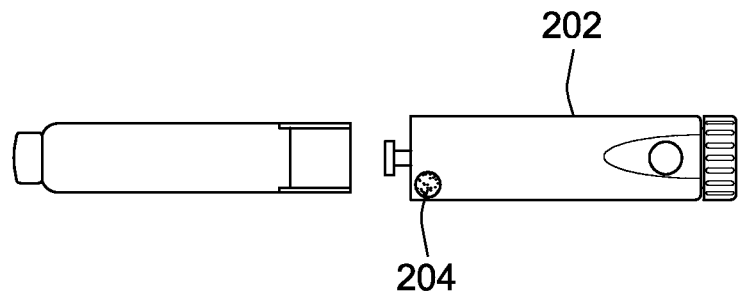

The light source 204 is preferably located at a proximal end of the cartridge 200, cartridge holder 208, or dose setting member 202. However, it should be understood that the light source 204 may be located at any visible area of the cartridge 200, cartridge holder 208, or dose setting member 202, as shown in FIGS. 2B-2G. For example, FIG. 2B shows the light source 204 being mounted onto or integral with the cartridge holder 208. The light source 204 may be mounted onto the cartridge holder 208 by any suitable fastening mechanism.

Figure 2E:
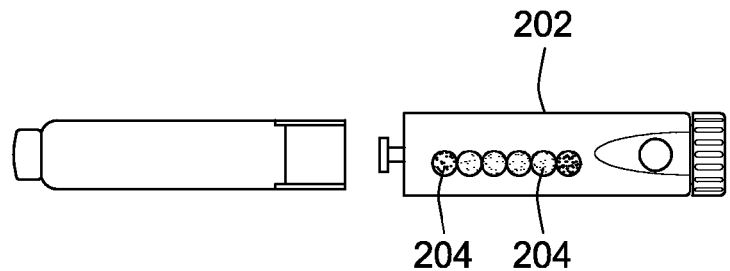
Figure 2F:
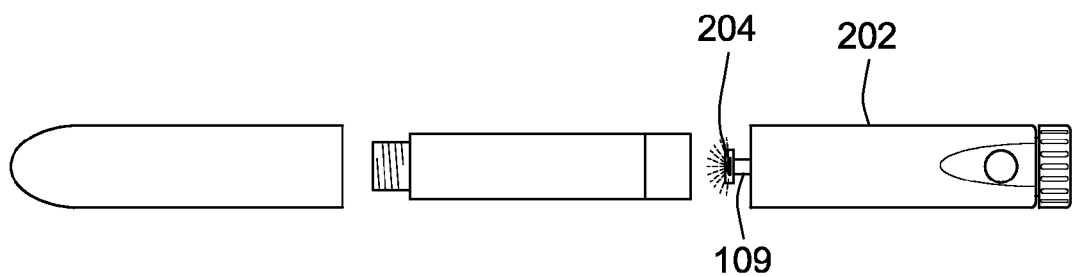
Figure 2G:
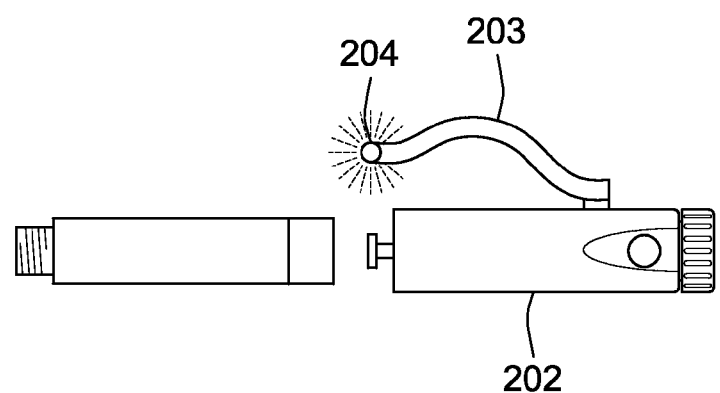

As another example, the light source 204 may be mounted onto the outer surface or inner surface of the dose setting member 202, as shown in FIGS. 2C-2G. Referring to FIG. 2E, the light source 204 may comprise a plurality of light sources. FIG. 2F shows the light source 204 attached to the piston 109 on the dose setting member 202. It should be understood that the light source 204 may be mounted onto the dose setting member 202 by any suitable fastening mechanism. For example, in one embodiment, the light source 204 may be attached to the dose setting member 202 by a flexible arm 203 to allow light to be directed to the site of injection or to a label.

Figure 4A:
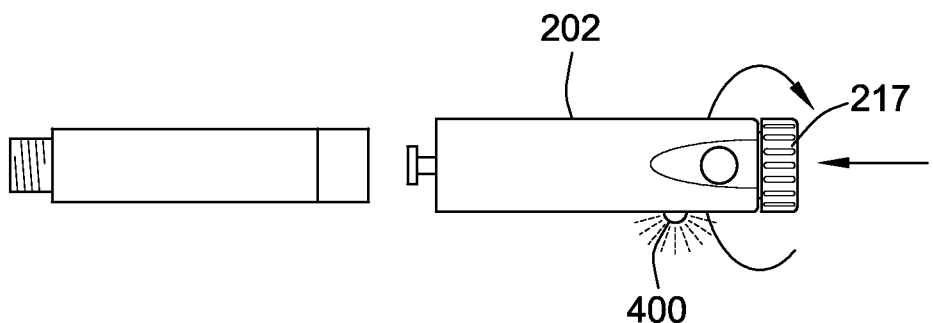
FIGS. 4A and 4B illustrate example trigger mechanisms that may be used with the delivery devices shown in FIGS. 2A-G.
Figure 4B:
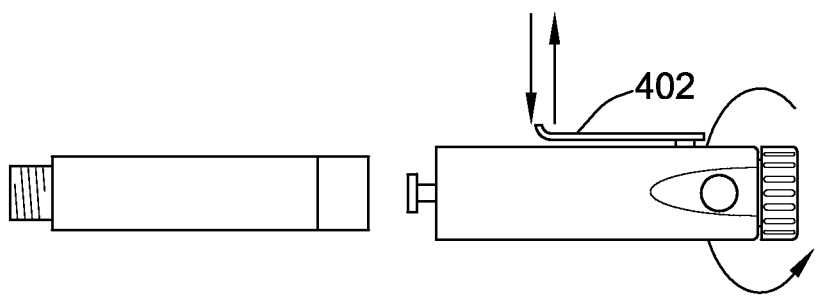

FIG. 3 shows a circuit 300 which includes the light source 204, a switch 302, a resistivity 303, and a power cell 301. The user may activate a trigger which closes the switch 302 and completes the circuit and illuminates the light source 204 when a cartridge 200 is correctly inserted into the drug delivery device 100. Examples of the trigger are shown in FIGS. 4A and 4B. FIG. 4A shows one example of a trigger which may include pushing or turning the dose setter 217 located on the dose setting member 202 to a specific start position, or pushing, pulling, or turning a separate knob 400 having an on/off function. Another example of a trigger, shown in FIG. 4B, may include turning or pulling a clip 402 located on the dose setting member 202.

In operation, when a user needs to take a drug, they may insert the cartridge 200 and cartridge holder 208 into a drug delivery device, such as drug delivery device 100. Once the cartridge 200 and holder 208 are inserted into the drug delivery device 100, the user activates a trigger which closes the switch 302 and illuminates the light source 204 when the correct cartridge 200 or cartridge holder 208 has been inserted. If the light source 204 is illuminated, the user can be confident that they have inserted the appropriate drug.

One advantage of the cartridge and cartridge holder system is that users become aware faster of optical signals, which prevents mix-up. Optical signals are more memorable to users, thereby preventing the accidental intake of the wrong type of drug by a patient.

Further, additional features or codings may be located on the cartridge 200 or cartridge holder 208 in addition to the light source 204 to further identify the type of drug contained in the cartridge 200. For example, symbols or other distinguishing features to indicate differences in the drug compared to other drugs may be included. Additionally, the cartridge 200 may be mechanically coded to the cartridge holder 208 or dose setting member 202 by protrusions or other physical elements.

Although aimed primarily at the insulin market, the coded cartridge holder may apply to other drugs. The disclosure may apply to various devices, including the following examples:

An injector pen with a cartridge (e.g. 3 ml cylindrical glass cartridge) and a separate holder.

An injector pen with a cartridge (e.g. 3 ml cylindrical glass cartridge) non removably retained in a holder, so that the holder will be disposed of with the primary pack.

An injector pen where the primary pack attaches directly to the pen, e.g. an injection moulded polymer cartridge.

Any drug delivery device, with any type of primary pack, e.g. inhaler, pouch.

The coding system results in a number of advantages. For example, the proposed coded cartridge holder arrangements assist a user to distinguish between medicaments, thereby helping to ensure that a drug delivery device 100 can only be used with a medicament 125 for which the device is intended. Therefore, with the system applied to a cartridge 200 to form a cartridge assembly, the cartridge assembly is prevented from being loaded into any other drug by loading a cartridge 200 with an incorrect fastening mechanism.

The coded cartridge holder 208 also results in a low cost coding mechanism since the proposed cartridge holders 208 do not require a large number of parts and can be manufactured in a cost effective manner. Moreover, there are quite a large number of different cartridge coding configurations between the cartridge 200, the cartridge holder 208, and the drug delivery device 100 that may be used. Consequently, with proposed coding schemes, a large number of medicaments can be distinguished from one another. In addition, with the coding schemes, if a user attempts to load an incorrect cartridge assembly into a cartridge holder 208 designed for a different cartridge assembly, the user will be alerted at an early stage of the assembly process.

In addition, the system can be used to prevent errors during manufacturing, when inserting cartridge assemblies into disposable cartridge holders 208 or disposable devices. With an incorrect drug (and hence incorrectly coded cartridge 200), the user is alerted at an early stage of assembly.

Exemplary embodiments have been described. Those skilled in the art will understand, however, that changes and modifications may be made to these arrangements without departing from the true scope and spirit of the present invention, which is defined by the claims.

The invention claimed is:

1. A drug delivery device comprising:
   a cartridge containing a drug;
   a cartridge holder to receive the cartridge; and
   a light source configured to illuminate and provide visual indication when the correct type of cartridge has been correctly paired with the cartridge holder or that the correct type of cartridge holder has been correctly paired with and inserted into the drug delivery device.

2. The drug delivery device of claim 1, wherein the correct cartridge or the correct cartridge holder contain the correct type of medicament.

3. The drug delivery device of claim 1, wherein the light source is located on the cartridge to visually indicate that the correct cartridge has been inserted into the drug delivery device.

4. The drug delivery device of claim 1, wherein the cartridge holder includes the light source to visually indicate that the correct cartridge holder has been inserted into the drug delivery device.

5. The drug delivery device of any of claim 1 further comprising a dose setting member which includes the light source.

6. The drug delivery device of claim 1 wherein the light source comprises one or more of a light emitting diode (LED), a surface mount diode (SMD), or an organic light emitting diode (OLED).

7. The drug delivery device of claim 1 wherein the light source is activated by a trigger upon insertion of the correct cartridge or the correct cartridge holder into the drug delivery device.

8. The drug delivery device of claim 1 wherein the light source comprises a blue light source to indicate that the inserted cartridge is correct for the drug delivery device.

9. The drug delivery device of claim 1 wherein the cartridge holder is removably secured to the cartridge.

10. The drug delivery device of claim 1 wherein the light source includes one or more colored lights that indicates that a specific drug is contained in the cartridge.

11. The drug delivery device of claim 10 wherein the light source includes at least two lights of different colors to indicate that a specific drug is contained in the cartridge.

12. The drug delivery device of claim 1 wherein the light source comprises only one light.

13. The drug delivery device claim 1 wherein the light source comprises a plurality of lights.

14. The drug delivery device of claim 1 further including a cartridge sleeve secured to the cartridge.

15. A drug delivery device comprising:
   a cartridge containing a drug;
   a cartridge holder to receive the cartridge; and
   a light source to visually indicate that the correct cartridge or the correct cartridge holder has been inserted into the drug delivery device and contains the correct type of medicament.

16. A drug delivery device comprising:
   a cartridge containing a drug;
   a cartridge holder to receive the cartridge; and
   a light source to visually indicate that the correct cartridge or the correct cartridge holder has been inserted into the drug delivery device,
   wherein the light source is located on the cartridge to visually indicate that the correct cartridge has been inserted into the drug delivery device or is located on the cartridge holder to visually indicate that the correct cartridge holder has been inserted into the drug delivery device.

17. A drug delivery device comprising:
   a cartridge containing a drug;
   a cartridge holder to receive the cartridge;
   a cartridge sleeve secured to the cartridge; and
   a light source to visually indicate that the correct cartridge or the correct cartridge holder has been inserted into the drug delivery device.

* * * * *